United States Patent [19]

Hase et al.

[11] 4,057,625
[45] Nov. 8, 1977

[54] COSMETIC EMULSIONS CONTAINING N-VINYLPYRROLIDONE/VINYL ALKYLCARBOXYLATE COPOLYMER

[75] Inventors: Brigitte Hase, Erkrath; Joachim Galinke, Langenfeld; Bernd Wegemund, Haan, all of Germany

[73] Assignee: Henkel Kommanditgesellschaft auf Aktien, Dusseldorf, Germany

[21] Appl. No.: 670,383

[22] Filed: Mar. 25, 1976

[30] Foreign Application Priority Data

Mar. 29, 1975 Germany .............................. 2514099

[51] Int. Cl.$^2$ .............................................. A61K 31/74
[52] U.S. Cl. .............................. 424/78; 424/DIG. 2; 424/168
[58] Field of Search ................................ 424/78, 168

[56] References Cited

U.S. PATENT DOCUMENTS

| | | | |
|---|---|---|---|
| 3,946,749 | 3/1976 | Papantoniou | 424/78 |
| 3,950,510 | 4/1976 | Adams | 424/78 |

FOREIGN PATENT DOCUMENTS

| | | | |
|---|---|---|---|
| 1,931,080 | 12/1970 | Germany | 424/78 |
| 7,797 | 4/1965 | Japan | 424/78 |

Primary Examiner—Dale R. Ore
Attorney, Agent, or Firm—Hammond & Littell

[57] ABSTRACT

Water-in-oil emulsions wherein the emulsifier consists essentially of copolymers of N-vinylpyrrolidone and a vinyl $C_{5-24}$ alkylcarboxylate (if desired with vinyl acetate) and the continuous phase is a cosmetically acceptable oily material can be prepared easily, safely and inexpensively. The emulsions are substantially odorless and are cosmetically acceptable for the care of the skin.

8 Claims, No Drawings

COSMETIC EMULSIONS CONTAINING N-VINYLPYRROLIDONE/VINYL ALKYLCARBOXYLATE COPOLYMER

FIELD OF THE INVENTION

The invention relates to cosmetic emulsions of the water-in-oil type having a content of polymers of N-vinylpyrrolidone with vinyl esters of alkylcarboxylic acids as emulsifiers and stabilizers. The invention includes the emulsions themselves and methods for the preparation thereof.

BACKGROUND OF THE INVENTION

In contrast to the production of oil-in-water emulsions, only a limited number of emulsifying agents are available, the best of which are becoming increasingly scarce, for producing cosmetic emulsions of the water-in-oil type. Wool fat and its derivatives are still some of the most important emulsifying agents for producing creams of the water-in-oil type. However, despite their uncontested advantages, wool fat and its derivatives such as lanolin have certain disadvantages. Thus, conventional water-in-oil emulsifying agents based on wool fat and its derivatives impart a strong intrinsic odor to creams which contain them. This, in turn, requires strong perfuming which frequently cannot be tolerated by persons with sensitive skin. However, this influencing of the quality of the cream by a strong intrinsic odor is not only peculiar to wool fat and its derivatives, but also extends to lanolin-free water-in-oil emulsufying agents based on animal sterols, particularly those based on cholesterol. Furthermore, low molecular weight emulsifying agents, together with the effective substances of the cream, can be absorbed by the skin, which is not desirable in all cases.

The most widely known water-in-oil emulsifying agents for cosmetic purposes include, in addition to the said emulsifying agents based on wool, wax alcohols and sterols, and the oleic acid esters of various polyols, such as glycerine, pentaerythritol, trimethylolpropane and sorbitol. However, due to the unsaturated character of their acid component, the oleic acid esters have various disadvantages with respect to their technical use, so there there is a genuine need for new and suitable water-in-oil emulsifying agents.

OBJECTS OF THE INVENTION

One object of the present invention is the development of a cosmetic emulsion or cream of the water-in-oil type which can be prepared easily and safely from inexpensive materials without need for costly emulsifying equipment.

Another object of the invention is the development of a cosmetic emulsion of the above type which is substantially odorless and which, therefore, can find general acceptance when containing only a small and harmless amount of perfume.

A further object of the invention is the development of such an emulsion which is stable at an acid, neutral and alkaline pH.

An additional object of the invention is the production of a cosmetic emulsion of the above type wherein the emulsifier is a copolymer or terpolymer of N-vinyl-pyrrolidone, a vinyl ester of a $C_{5-24}$ alkyl carboxylic acid and, if desired, vinyl acetate, and a cosmetically acceptable oily material as the continuous phase.

The principal object of the present invention is thus the production of a cosmetic emulsion of the water-in-oil type consisting essentially of (1) from 2% to 20% by weight of a polymeric emulsifier capable of forming water-in-oil creams consisting of a copolymer of (a) N-vinyl pyrrolidone, (b) vinyl carboxylates of the formula:

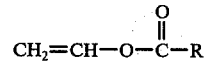

wherein R is an alkyl having from 5 to 24 carbon atoms, and (c) vinyl acetate wherein the molar ratios of [(a) + (c)]:(b) are from 1:2 to 1:20 and the molar ratios of (c):(a) are 0:1 to 3:1, (2) from 20% to 75% by weight of water, and (3) the remainder to 100% by weight of a cosmetically acceptable oily material.

These and other objects of the present invention will become more apparent as the description thereof proceeds.

DESCRIPTION OF THE INVENTION

It has now been discovered that the objections of the prior emulsifiers have been overcome and the above objects have been achieved by the discovery of cosmetic emulsions of the water-in-oil type having a content of 2% to 20% by weight of a polymer from N-vinylpyrrolidone, a vinyl ester of an alkylcarboxylic acid having 5 to 24 carbon atoms in the alkyl (hereinafter termed a "vinyl $C_{5-24}$ alkylcarboxylate") and, if required, vinyl acetate, from 20% to 75% by weight of water, and vegetable or animal fats, waxes, fatty alcohols, hydrocarbons and other hydrophobic auxiliary substances normally present in cosmetic emulsions.

More particularly, the present invention relates to a cosmetic emulsion of the water-in-oil type consisting essentially of (1) from 2% to 20% by weight of a polymeric emulsifier capable of forming water-in-oil creams consisting essentially of a copolymer of (a) N-vinylpyrrolidone, (b) one or more vinyl $C_{5-24}$ alkylcarboxylates of the formula:

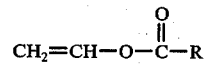

wherein R is an alkyl group having from 5 to 24 carbon atoms and, optionally (c) vinyl acetate, wherein the molar ratios of [(a) + (c)]:(b) are from 1:2 to 1:20, preferably 1:3 to 1:8, and the molar ratios of (c):(a) are 0:1 to 3:1, (2) from 20% to 75% by weight of water, and (3) the remainder to 100% by weight of a cosmetically acceptable oily material.

The copolymers or terpolymers from N-vinylpyrrolidone, one or more vinyl $C_{5-24}$ alkylcarboxylates and, if required, vinyl acetate, usable as emulsifying agents in the cosmetic emulsions in accordance with the invention, can be produced in a generally known manner by one processing step under the normal conditions of free radical polymerization. Polymerization can be carried out in nonpolar solvents, such as benzene or toluene, or in polar solvents, such as methanol or tetrahydrofurane, by means of peroxides, such as dibenzoyl peroxide or lauroyl peroxide, and azo compounds, such as azobisisobutyronitrile as free-radical polymerization catalysts.

The technical production is effected to best advantage in the form of solution polymerization in such solvents which only dissolve the monomers but not the polymers produced (precipitation polymerization), especially since polymers are produced which are satisfactorily precipitable and which are virtually free from monomers (J. Scheiber, Chemie and Technologie der Kunstlichen Harze, Vol. I, pp. 362 ff, 1961).

Monomeric starting compounds of the polymers which may be mentioned in addition to N-vinylpyrrolidone and, if required, vinyl acetate, are, for example:
vinyl caproate
vinyl caprylate
vinyl pelargonate
vinyl caprate
vinyl laurate
vinyl myristate
vinyl palmitate
vinyl isopalmitate
vinyl stearate
vinyl arachidate
vinyl behenate.

Particular importance is attached to the vinyl esters of carboxylic acids having 8 to 14 carbon atoms, for example:
vinyl caproate
vinyl pelargonate
vinyl caprate, and particularly
vinyl laurate and vinyl myristate.

In the copolymers or terpolymers usable in accordance with the invention, the molar ratios of the monomers (N-vinylpyrrolidone + vinyl acetate):vinyl $C_{5-24}$ alkyl carboxylate are 1:2 to 1:20 and preferably 1:3 to 1:8, wherein the molar ratio vinyl acetate:N-vinylpyrrolidone is 0:1 to 3:1.

The copolymers or terpolymers present in emulsions of the invention have average molecular weights between 2,000 and 100,000. Those having average molecular weights between 3,000 and 20,000 are particularly suitable in view of the easy processability and the quality of the emulsions obtained. Polymers having molecular weights within these ranges can be prepared in known manner by varying the amount of catalyst and the nature and amount of the solvent, and by adding polymerization or molecular weight regulators.

The emulsions in accordance with the invention are manufactured in a simple and known manner by dissolving the copolymers or terpolymers, acting as emulsifying agents, in the oily phase at an elevated temperature where the components are fluid (approximately 60° C to 70° C). Subsequently the desired quantity of water heated to approximately 60° C to 65° C is added. An emulsion rapidly forms which is allowed to cool with continued stirring. Cosmetically effective amounts of further constituents of the cosmetic emulsions to be manufactured, such as skin moisture regulators (moisturizing agents), vegetable extracts of effective substances, vitamins, hormones, pigments, salts, perfume oil, ultraviolet absorbers, dyes, etc., in amounts less than 10% of the weight of the emulsion, are advantageously dissolved or distributed in the phase which bests absorbs the respective substances. The required quantity of emulsifying agent is 2% to 20% and preferably 5% to 10% of the total weight of the emulsion. The amount of water to be incorporated is 20% to 75%, and preferably 45% to 65%, of the weight of the emulsion.

Products conventionally used, such as animal and vegetable oils and fats, synthetic esters of higher fatty acids with alkanols, higher fatty alcohols, waxes, so-called mineral fats and oils, such as paraffin oil, "Vaseline" ®, ceresine, silicone oils and silicone fats are suitable as the oily phase of the cosmetic emulsions in accordance with the invention. They should have melting points above 30° C and be substantially solids at room temperature.

German Offenlegungsschrift (DOS) No. 2,116,787 has already described the use of water-in-oil emulsifying agents in the form of sequence polymers which have at the same time at least one lipophilic sequence and one hydrophilic sequence. Each of the sequences should have the properties of the corresponding homopolymers. These sequence polymers are obtained by anionic polymerization which places high demands on the purity of the substances used, and requires working at low temperatures under protective gas and increased safety precautions when handling spontaneously inflammable catalysts. In contrast to this, the emulsifying agents required for producing the emulsions in accordance with the present invention can be manufactured in a simple manner.

In accordance with the German Offenlegungsschrift (DOS) No. 1,745,216, copolymers comprising a monomer having a lipophilic chain and a monomer having a carboxylic acid anhydride function are proposed as emulsifying agents for water-in-oil emulsions. However, such products are sensitive to hydrolysis and, to avoid this disadvantage, a further processing step in addition to polymerization is necessary in order to convert them into a more stable form.

In general, the emulsions in accordance with the present invention can also be used by persons having a sensitive skin. Since they do not have any appreciable intrinsic odor, they do not require heavy perfuming which, in turn, has an advantageous effect upon the compatibility and also saves cost.

Furthermore, the emulsions in accordance with the invention are distinguished by a low sensitivity to acid, thus rendering it possible to incorporate acidic raw materials therein, such as organic acids. A further very advantageous property of the emulsions in accordance with the invention is their high resistance to temperature, which enables them to withstand a thermal stress of 50° C for a period of 6 weeks without any detrimental effects.

The following examples are intended to further explain the invention, but without limiting the invention to these examples.

EXAMPLES

The following illustrates the production of a copolymer suitable for use in cosmetic emulsions of the invention.

EXAMPLE 1

N-Vinylpyrrolidone/vinyl laurate copolymer (1:3 molar ratio)

To a solution of 27.75 gm (0.25 mol) of N-vinylpyrrolidone and 169.5 gm (0.75 mol) of vinyl laurate in 460 gm of methanol were added 6 gm of azobisisobutyronitrile as catalyst. The resulting reaction mixture was agitated for 6 hours at 60° C, during which time the copolymer precipitated. After completion of the reaction, the methanol was distilled off and the polymer was washed a few times with fresh methanol. The yield was 176.5 gm (90% of theory) of N-vinylpyrrolidone/vinyl laurate copolymer (1:3 molar ratio).

The other copolymers or terpolymers in the examples given below were produced in corresponding manner.

EXAMPLE 2

Cosmetic emulsion based on Vaseline ®

A mixture of 10 gm of N-vinylpyrrolidone/vinyl laurate copolymer (1:3 molar ratio) and 40 gm of Vaseline ® was heated to 65° C. 50 gm of water were added at 65° C. with stirring to the melt. The emulsion formed was allowed to cool with continued agitation. The emulsion readily formed with only manual stirring and on cooling was a cream. The cream was stable for several months and did not exhibit any change even after six weeks of storage at 50° C. This basic cream can be used to produce various skin creams by adding cosmetically effective amounts of various cosmetically effective substancs and perfumes.

By way of example, the following copolymers can be used with the same satisfactory results instead of the above-described N-vinylpyrrolidone/vinyl laurate copolymer:

| Copolymer | Molar Ratio |
|---|---|
| N-vinylpyrrolidone/vinyl laurate | (1:4) |
| N-vinylpyrrolidone/vinyl caprylate | (1:15) |
| N-vinylpyrrolidone/vinyl caproate | (1:20) |
| N-vinylpyrrolidone/vinyl caprate | (1:8) |
| N-vinylpyrrolidone/vinyl caprate | (1:10) |
| N-vinylpyrrolidone/vinyl myristate | (1:4) |
| N-vinylpyrrolidone/vinyl myristate | (1:6) |
| N-vinylpyrrolidone/vinyl stearate | (1:2) |
| N-vinylpyrrolidone/vinyl isopalmitate | (1:3) |

EXAMPLE 3

Cosmetic emulsion based on hardened peanut oil/decyl oleate mixture

A mixture of 4 gm of N-vinylpyrrolidone/vinyl laurate copolymer (1:6 molar ratio), 40 gm of hardened peanut oil/decyl oleate mixture (90:10 by weight), 3 gm of beeswax and 3 gm of glyceryl monooleate were melted together to 70° C. To this were added 50 gm of water at 65° C with continuous stirring and the resulting emulsion was allowed to cool to room temperature with continued agitation. A cream was obtained the stability properties of which were substantially the same as those of the cream of Example 2.

Various skin creams based on this basic cream can be produced by incorporating further effective substances such as skin moisturizers, vegetable extracts, and perfume oils.

By way of example, the following copolymers can be used with the same satisfactory results instead of the N-vinylpyrrolidone/vinyl laurate copolymer:

| Copolymer | Molar ratio |
|---|---|
| N-vinylpyrrolidone/vinyl myristate | (1:3) |
| N-vinylpyrrolidone/vinyl laurate | (1:3) |
| N-vinylpyrrolidone/vinyl myristate | (1:8) |
| N-vinylpyrrolidone/vinyl palmitate | (1:4) |
| N-vinylpyrrolidone/vinyl behenate | (1:2) |
| N-vinylpyrrolidone/vinyl isopalmitate | (1:3) |

EXAMPLE 4

Cosmetic emulsions based on Vaseline ®/decyl oleate mixture

A mixture of 7 gm of N-vinylpyrrolidone/vinyl acetate/vinyl laurate terpolymer (2:1:10 molar ratio), 10 gm of Vaseline ®, 15 gm of decyl oleate, 3 gm of beeswax, and 2 gm of calcium stearate were melted together by heating to 65° C. To the melt were added 63 gm of water at 65° C with stirring, and agitation was continued until an emulsion was obtained. On cooling the emulsion, a cream was obtained, the stability of which was largely similar to those of the two creams described above.

A large number of cosmetic creams based on this basic cream can be produced by incorporating into the cream cosmetically effective amounts of cosmetic substances and perfume oils.

By way of example, the following terpolymers can be used with the same satisfactory results instead of the N-vinylpyrrolidone/vinyl acetate/vinyl laurate terpolymer (2:1:10 molar ratio):

| Terpolymer | Molar ratio |
|---|---|
| N-vinylpyrrolidone/vinyl acetate/vinyl laurate | (3:1:12) |
| N-vinylpyrrolidone/vinyl acetate/vinyl myristate | (2:1:10) |
| N-vinylpyrrolidone/vinyl acetate/vinyl caprate | (2:1:15) |
| N-vinylpyrrolidone/vinyl acetate/vinyl laurate | (1:1:12) |
| N-vinylpyrrolidone/vinyl acetate/vinyl myristate | (1:1:10) |
| N-vinylpyrrolidone/vinyl acetate/vinyl stearate | (2:1:6) |
| N-vinylpyrrolidone/vinyl acetate/vinyl myristate | (1:2:10) |
| N-vinylpyrrolidone/vinyl acetate/vinyl laurate | (1:3:8) |
| N-vinylpyrrolidone/vinyl acetate/vinyl isopalmitate | (2:1:10) |

EXAMPLE 5

Cosmetic emulsions based on hardened peanut oil

A mixture of 6 gm of N-vinylpyrrolidone/vinyl acetate/vinyl laurate terpolymer (1:1:8 molar ratio) and 44 gm of hardened peanut oil was melted together by heating to 65° C. To this were added 50 gm of water at 65° C with stirring, and the emulsion was allowed to cool with continuous stirring. The components emulsified easily forming a cream which was about as stable as the previously mentioned creams.

The cream can act as a basic cream for various cosmetic preparations.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A cosmetic emulsion of the water-in-oil type consisting essentially of (1) from 2% to 20% by weight of a polymeric emulsifier capable of forming water-in-oil creams consisting of a copolymer of (a) N-vinylpyrrolidone, (b) at least one vinyl $C_{5-24}$ alkylcarboxylate of the formula

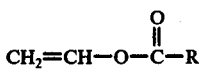

wherein R is alkyl having from 5 to 24 carbon atoms, and (c) vinyl acetate wherein the molar ratios of [(a) + (c)]:(b) are from 1:2 to 1:20 and the molar ratios of (c):(a) are 0:1 to 3:1, (2) from 20% to 75% by weight of water, and (3) the remainder to 100% by weight of a cosmetically acceptable oily material.

2. The cosmetic emulsion of claim 1 wherein said cosmetically acceptable oily phase has a melting point above 30° C and is selected from the group consisting of vegetable fat, animal fat, wax, higher fatty alcohol, mineral oil and silicone oil.

3. The cosmetic emulsion of claim 1 wherein said polymeric emulsifier is present in an amount of from 5% to 10% by weight and said water is present in an amount of from 45% to 65% by weight.

4. The cosmetic emulsion of claim 1 wherein R is alkyl having from 8 to 14 carbon atoms.

5. The cosmetic emulsion of claim 1 wherein the molar ratio of (a) + (c):(b) is from 1:3 to 1:8.

6. The cosmetic emulsion of claim 1 wherein said polymeric emulsifier has an average molecular weight of from 2,000 to 100,000.

7. The cometic emulsion of claim 6 wherein said average molecular weight is from 3,000 to 20,000.

8. In the process of preparing a cosmetic emulsion of the water-in-oil type comprising mixing an emulsifyingly effective amount of an emulsifier capable of forming water-in-oil creams with a cosmetically acceptable oily material in the liquid phase at elevated temperatures, mixing from 20% to 75% by weight of water thereto, cooling with agitation and recovering a cosmetic emulsion of the water-in-oil type, the improvement consisting of mixing from 2% to 20% by weight of a copolymer of (a) N-vinylpyrrolidone, (b) at least one vinyl $C_{6-24}$ alkylcarboxylate of the formula

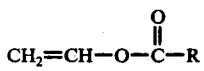

wherein R is alkyl having 5 to 24 carbon atoms, and (c) vinyl acetate, wherein the molar ratios of [(a) + (c)]:(b) are from 1:2 to 1:20 and the molar ratios of (c):(a) are 0:1 to 3:1, as said emulsifier.

* * * * *